(12) United States Patent
Kerr

(10) Patent No.: US 10,117,708 B2
(45) Date of Patent: *Nov. 6, 2018

(54) ABLATION NEEDLE INCLUDING FIBER BRAGG GRATING

(71) Applicant: COVIDIEN LP, Mansfield, MA (US)

(72) Inventor: Duane E. Kerr, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,859

(22) Filed: Aug. 8, 2017

(65) Prior Publication Data

US 2017/0333117 A1    Nov. 23, 2017

Related U.S. Application Data

(60) Continuation of application No. 15/404,921, filed on Jan. 12, 2017, now Pat. No. 9,730,754, which is a continuation of application No. 15/015,674, filed on Feb. 4, 2016, now Pat. No. 9,549,776, which is a division of application No. 13/803,636, filed on Mar. 14, 2013, now Pat. No. 9,265,573.

(60) Provisional application No. 61/673,644, filed on Jul. 19, 2012.

(51) Int. Cl.
| | |
|---|---|
| *A61B 18/18* | (2006.01) |
| *A61B 18/14* | (2006.01) |
| *A61B 18/12* | (2006.01) |
| *G01L 1/24* | (2006.01) |
| *G01K 11/32* | (2006.01) |
| *A61B 18/00* | (2006.01) |
| *A61B 90/00* | (2016.01) |
| *A61B 17/00* | (2006.01) |

(52) U.S. Cl.
CPC ...... *A61B 18/1477* (2013.01); *A61B 18/1206* (2013.01); *G01K 11/3206* (2013.01); *G01L 1/246* (2013.01); *A61B 2017/00061* (2013.01); *A61B 2017/00115* (2013.01); *A61B 2018/00577* (2013.01); *A61B 2018/00791* (2013.01); *A61B 2090/064* (2016.02)

(58) Field of Classification Search
USPC ..................................................... 606/41, 44
See application file for complete search history.

(56) References Cited

U.S. PATENT DOCUMENTS

| | | |
|---|---|---|
| 5,958,605 A | 9/1999 | Montcalm et al. |
| 6,359,969 B1 | 3/2002 | Shmaenok |
| 6,614,505 B2 | 9/2003 | Koster et al. |

(Continued)

*Primary Examiner* — Nicole F Johnson

(57) ABSTRACT

A surgical device is disclosed, and includes a probe having a handle assembly and an electrode assembly extending distally therefrom. An optical member is disposed on the probe and has a first set of light transmitting properties corresponding to a first set of physical parameters of the probe. The probe is configured to transition to a second set of physical parameters, the second set of physical parameters being different from the first set of physical parameters. The optical member is configured to transition from the first set of light transmitting properties to a second set of light transmitting properties, the second set of light transmitting properties corresponding to the second set of physical parameters, the second set of light transmitting properties being different from the first set of light transmitting properties.

17 Claims, 7 Drawing Sheets

(56) References Cited

U.S. PATENT DOCUMENTS

| | | |
|---|---|---|
| 7,393,354 B2 | 7/2008 | Buchman, II et al. |
| 7,553,686 B2 | 6/2009 | George et al. |
| 9,265,573 B2 | 2/2016 | Kerr |
| 9,549,776 B2 | 1/2017 | Kerr |
| 9,730,754 B2 | 8/2017 | Kerr |
| 2002/0084425 A1 | 7/2002 | Klebanoff et al. |
| 2004/0121134 A1 | 6/2004 | Bijkerk et al. |
| 2005/0096713 A1* | 5/2005 | Starkebaum ....... A61B 18/1492 607/100 |
| 2005/0283148 A1* | 12/2005 | Janssen ............ A61B 18/1477 606/34 |
| 2006/0048866 A1 | 3/2006 | Takada et al. |
| 2006/0219958 A1 | 10/2006 | Wassink |
| 2006/0224053 A1 | 10/2006 | Black et al. |
| 2007/0040999 A1 | 2/2007 | Wilhelmus Van Herpen et al. |
| 2008/0077200 A1 | 3/2008 | Bendett et al. |
| 2008/0125775 A1 | 5/2008 | Morris |
| 2009/0159808 A1 | 6/2009 | Bowering et al. |
| 2010/0190113 A1 | 7/2010 | Murakami et al. |
| 2010/0331834 A1 | 12/2010 | Peterson et al. |
| 2011/0060325 A1 | 3/2011 | Bonn |
| 2011/0224825 A1* | 9/2011 | Larkin ................ B25J 19/025 700/254 |
| 2011/0259374 A1 | 10/2011 | Nakayama |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0307224 A1 | 12/2012 | Yakunin et al. |

* cited by examiner

ABLATION NEEDLE INCLUDING FIBER BRAGG GRATING

CROSS-REFERENCE TO RELATED APPLICATION

The present application is a continuation of U.S. patent application Ser. No. 15/404,921, filed on Jan. 12, 2017, now U.S. Pat. No. 9,730,754, which is a continuation of U.S. patent application Ser. No. 15/015,674, filed on Feb. 4, 2016, now U.S. Pat. No. 9,549,776, which is a divisional of U.S. patent application Ser. No. 13/803,636 filed on Mar. 14, 2013, now U.S. Pat. No. 9,265,573, which claims the benefit of and priority to U.S. Provisional Patent Application No. 61/673,644, filed on Jul. 19, 2012. The entire disclosures of all of the foregoing applications are incorporated herein by reference.

BACKGROUND

Technical Field

The present disclosure relates generally to an electrosurgical device, and more particularly to one or more probes including a needle and an electrode for treating tissue, as well as an optical fiber for the detection of the changing physical characteristics of the probe.

Background of Related Art

Electrosurgical instruments are commonly used in open and minimally invasive surgical procedures. Because nerve and muscle stimulation cease at 100,000 cycles per second (100 kHz), electrosurgical procedures can be performed safely at radio frequencies ("RF") above 100 kHz. At these frequencies, electrosurgical energy can pass through a patient with minimal neuromuscular stimulation.

Electrosurgery involves application of high RF electrical current to a surgical site to cut, ablate, or coagulate tissue. In bipolar electrosurgery, one of a pair of electrodes of an instrument is an active electrode and the other a return electrode. The return electrode is placed in close proximity to the active electrode such that an electrical circuit is formed between the two electrodes, e.g., electrosurgical forceps, graspers, pencils, and the like. In this manner, the applied electrical current is limited to the body tissue positioned between the electrodes. When the electrodes are sufficiently separated from one another, the electrical circuit is open and thus incidental contact of body tissue with either of the separated electrodes inhibits current flow.

In monopolar electrosurgery, a source or active electrode delivers RF energy from the electrosurgical generator to the tissue and a return electrode carries the current back to the generator. The source electrode is typically part of the surgical instrument held by the surgeon and applied to the tissue to be treated. A patient return electrode is placed remotely from the active electrode to carry the current back to the generator.

In both monopolar and bipolar applications, RF energy may be delivered to targeted tissue by a probe. In use, the probe typically includes a needle and is advanced through tissue to a desired position either prior to or during application of energy to tissue. However, due to the remote placement of the probe or needle with respect to an operator, it is challenging to monitor the changing conditions of the site of the electrosurgical procedure. Accordingly, it would be desirable to provide such a probe having the capability to provide feedback to an operator on the performance and the condition of the probe and surrounding tissue, e.g., temperature, mechanical strain, and other relevant characteristics. It would be further desirable to provide a thermal profile or map of a tissue site.

SUMMARY

The present disclosure relates to an electrosurgical apparatus and methods for performing electrosurgical procedures. More particularly, the present disclosure relates to thermal ablation of tissue. As is traditional, the term "distal" refers herein to an end of a device that is farther from an operator, and the term "proximal" refers herein to the end of a device which is closer to the operator.

As used herein, "bipolar" electrosurgery involves one of a pair of electrodes being an active electrode and the other electrode being a return electrode. The return electrode is placed in close proximity to the active electrode such that an electrical circuit is formed between the two electrodes.

Further, "monopolar" electrosurgery involves the use of a source or active electrode to deliver RF energy from an electrosurgical generator to tissue and a return electrode carries the current back to the electrosurgical generator. A patient return electrode is placed remotely from the active electrode to carry the current back to the generator.

Energy-based tissue therapies such as ablation techniques are used clinically and in the operating room for therapeutic and surgical purposes. Such techniques eliminate tissue using energy sources such as laser, microwave, radiofrequency, high-intensity focused ultrasound, cryotherapy (such as freezing below −20° C.), conductive heating, and the like. The presently disclosed devices may be used with all of the above techniques and modalities.

According to one aspect of the present disclosure, a surgical device is disclosed, and includes a probe having a handle assembly and an electrode assembly extending distally therefrom. An optical member is disposed on the probe and has a first set of light transmitting properties corresponding to a first set of physical parameters of the probe. The probe is configured to transition to a second set of physical parameters, the second set of physical parameters being different from the first set of physical parameters. The optical member is configured to transition from the first set of light transmitting properties to a second set of light transmitting properties, the second set of light transmitting properties corresponding to the second set of physical parameters, the second set of light transmitting properties being different from the first set of light transmitting properties.

According to another aspect of the present disclosure, the first and second sets of physical parameters are selected from the group consisting of temperature, mechanical strain, and combinations thereof. In a further aspect, the first and second sets of light transmitting properties include transmittance.

In another aspect of the present disclosure, a surgical device includes a probe adapted to connect to an electrosurgical generator, the probe including a handle assembly and an electrode assembly including a needle, the needle extending distally from the handle assembly. A sensor assembly is operably coupled to the probe. The sensor assembly includes an optical member and a light source, the optical member is configured to transmit light from the light source. A change in the transmission of light through the optical member corresponds to a changed condition of the probe.

In another aspect of the present disclosure the changed condition of the probe includes at least one of a change in temperature or a change in mechanical strain. The plurality of probes may be arranged such that the plurality of probes are configured to detect a respective plurality of changed conditions. The surgical device may include a visual display system configured to display at least one changed condition of the probe.

In a further aspect of the present disclosure the optical member is at least partially disposed within the probe.

In another aspect of the present disclosure, the optical member includes a Bragg grating. The Bragg grating reflects a first wavelength of light transmitted from the light source. In the changed condition, the Bragg grating reflects a second wavelength of light from the light source, the second wavelength of light being different from the first wavelength of light. The Bragg grating includes a plurality of segments disposed in a periodic pattern. Each of the plurality of segments has a predetermined refractive index.

In a further aspect of the present disclosure, the optical member defines a length and has a refractive index that varies along the length of the optical member.

In another aspect of the present disclosure, a method of measuring characteristics of an electrosurgical device is disclosed, and includes providing an electrosurgical device including a probe having a handle assembly and an electrode assembly extending therefrom. A light transmissive member is disposed on the probe, and the light transmissive member includes a spaced plurality of segments configured to reflect at least one wavelength of light and transmit at least one wavelength of light. Light is projected through the light transmissive member, and a first wavelength of light transmitted through the light transmissive member is measured. The probe is inserted into tissue such that a force is applied to the probe, and a second wavelength of light transmitted through the light transmissive member after the force is applied is measured. The first wavelength of light is compared to the second wavelength of light to determine a change in spacing between the plurality of segments resulting from the force.

In a further aspect of the present disclosure, the step of comparing the first wavelength of light to the second wavelength of light includes determining the amount of mechanical strain experienced by the probe. In another aspect of the present disclosure, the step of providing an electrosurgical device includes supplying a current between the electrode assembly and a return electrode. In yet another aspect of the present disclosure, the step of providing an electrosurgical device includes providing a plurality of probes. In a further aspect of the present disclosure, the method further includes the step of comparing the respective first wavelength of light to the respective second wavelength of light of each of the respective probes. In another aspect of the present disclosure, the method further includes the step of generating a thermal profile from the plurality of probes.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

The present disclosure provides for a system and method for providing a variety of sensor feedback regarding operation of an electrosurgical device including a probe. Such feedback includes, but is not limited to, temperature of the probe and the surrounding tissue, pressure exerted on the probe, position and pressure of various mechanical components of the electrosurgical device, and identification information corresponding to the electrosurgical device. Although the feedback system according to present disclosure is described below with respect to an ablation probe, the system may be utilized in a variety of surgical instruments, including but not limited to, open surgical forceps, tweezer-type devices, graspers, staplers, pencils, and the like. Although this configuration is typically associated with instruments for use in laparoscopic or endoscopic surgical procedures, various aspects of the present disclosure may be practiced with traditional open instruments and in connection with endoluminal procedures as well.

Figure 1:
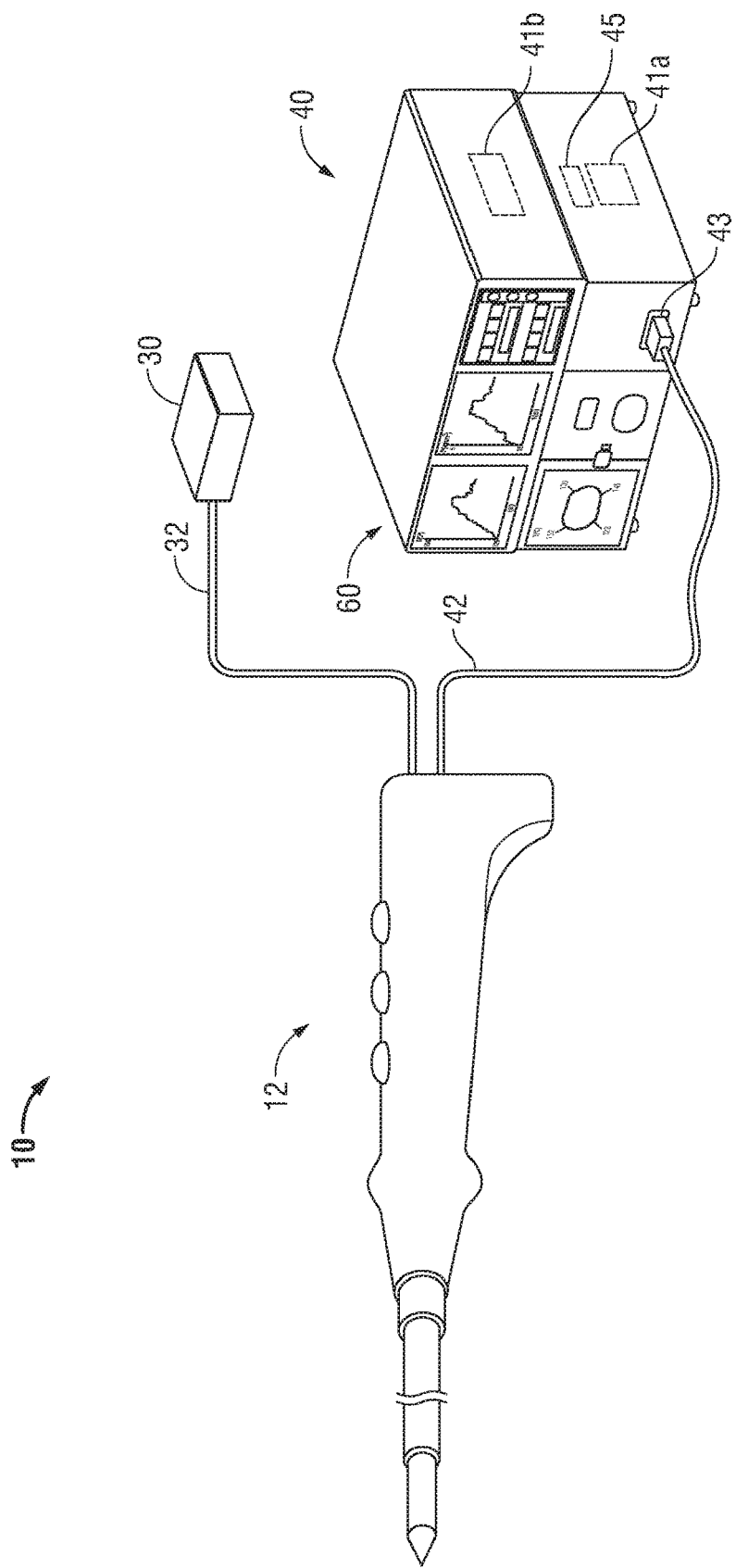
FIG. 1 is a perspective view of an embodiment of an electrosurgical system according to the present disclosure.

With reference to FIG. 1, an embodiment of an electrosurgical system 10 is shown, and includes an ablation probe 12. Probe 12 may have a variety of configurations, and is electrically coupled with a source of electrosurgical energy such as electrosurgical generator 40. The generator 40 may be any suitable generator, such as the LIGASURE® Vessel Sealing Generator and the FORCETRIAD® Generator as sold by Surgical Solutions of Boulder, Colo. Other suitable electrosurgical generators as are known in the art may be used with probe 12. The generator 40 includes a display system 60, which may be integrally formed with the generator 40, e.g., disposed in the same housing, and will be described in further detail below.

A cable 42 extends between the probe 12 and the generator 40. A connector 43 is disposed on an end of the cable 42 and interfaces with generator 40 such that the probe 12 may be selectively coupled and decoupled electrically from the generator 40. In some embodiments, the cable 42 includes additional connectors 43 such that probe 12 may be selectively coupled or decoupled to the cable 42 in this manner. Additionally, a cooling fluid source 30 may be coupled to probe 12 through one or more fluid hoses 32, as will be described further below.

Figure 2:
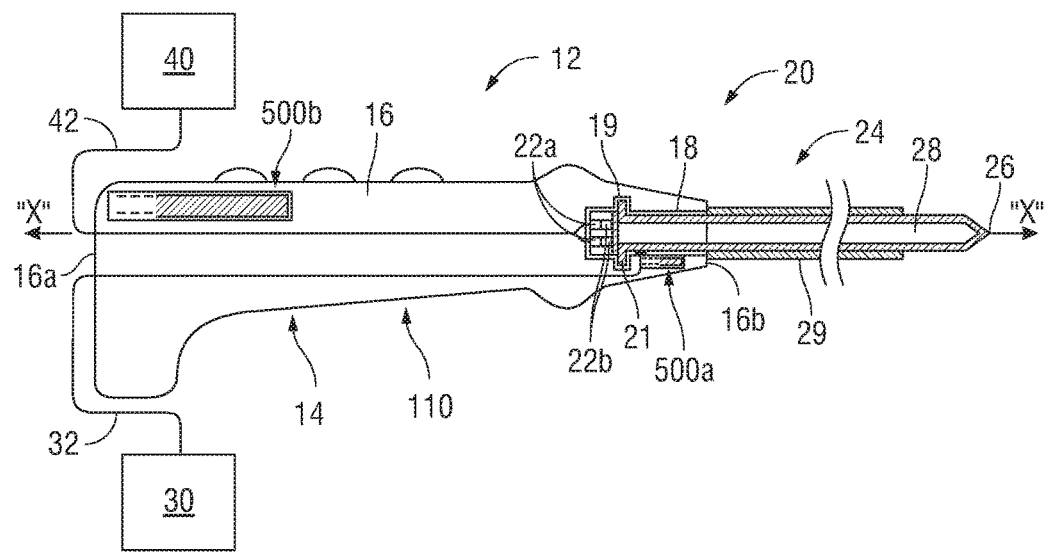
FIG. 2 is a side cross-sectional view of the probe of FIG. 1 connected to a generator and a cooling source.

With additional reference to FIG. 2, probe 12 generally includes a handle assembly 14 and an electrode assembly 20 releasably engagable with and extending distally from handle assembly 14. Although only one electrode assembly 20 is shown, additional electrode assemblies 20, either similar to or different from electrode assembly 20, may be provided for releasable engagement with handle assembly 14. The probe 12 may be configured for delivery of any type of energy, including, but not limited to, electrosurgical, microwave, laser, ultrasound, thermal (e.g., cryotherapy), and combinations thereof.

Handle assembly 14 includes a housing 16 which may be ergonomically or otherwise configured to facilitate the grasping and manipulation of housing 16 by an operator to position electrode assembly 20 as desired. Housing 16 is formed from an insulative material and defines proximal and distal ends 16a, 16b, respectively. Proximal end 16a of housing 16 is configured to receive cable 42 from generator 40, and one or more fluid hoses 32 from cooling fluid source 30, respectively, for supplying energy and cooling fluid, respectively, to electrode assembly 20. Distal end 16b of housing 16 defines an engagement recess 18 configured to receive a proximal portion of electrode assembly 20 therein for engaging electrode assembly 20 and handle assembly 14 to one another. More specifically, engagement recess 18 of housing 16 defines one or more notches 19 therein that are configured to engage protrusions 21 extending outwardly from a proximal end of electrode assembly 20 upon insertion of electrode assembly 20 into engagement recess 18 of housing 16 for releasably mechanically engaging electrode assembly 20 and handle assembly 14 to one another. Other releasable engagement mechanisms, e.g., snap-fit engagements, threaded-engagements, friction-fit engagements, etc., are also contemplated.

With continued reference to FIGS. 1-2, handle assembly 14 further includes a pair of electrical contacts 22a (although greater or fewer contacts are also contemplated) disposed on the proximal end of engagement recess 18 that are configured to electrically couple to corresponding electrical contacts 22b positioned on the proximal end of electrode assembly 20, thereby establishing electrical communication between handle assembly 14 and electrode assembly 20 upon mechanical engagement of handle assembly 14 and electrode assembly 20 to one another. One or more transmission wires may extend through housing 16 of handle assembly 14 to couple electrical contacts 22a to cable 42, and ultimately to generator 40 (not shown). As such, power and/or control signals may be transmitted between generator 40 and electrode assembly 20 via the pairs of electrical contacts 22a, 22b. In particular, electrical contacts 22a, 22b may be configured for establishing a conductive path for transmission of energy between generator 40 and electrode assembly 20. As such, upon activation, energy can be transmitted from generator 40 to electrode assembly 20, e.g., via cable 42, contacts 22a, 22b, and ultimately, conducted through tissue to ablate or otherwise treat tissue.

One of the pairs of contacts 22a, 22b may be utilized for identifying or verifying the identification of the particular type of electrode assembly 20 engaged with handle assembly 14. This feature helps ensure that an acceptable electrode assembly 20 has been engaged to handle assembly 14 and/or that the proper energy delivery and control parameters for the particular electrode assembly 20 engaged with handle assembly 14 are provided by generator 40. Additionally or alternatively, the same or a different pair of contacts 22a, 22b may be utilized to indicate the number of times that the particular electrode assembly 20 engaged with handle assembly 14 has been used. Further, the operation of cooling fluid source 30 may also be at least partially dependent upon the particular type of electrode assembly 20 detected. Thus, identifying information for the particular type of electrode assembly 20 engaged to handle assembly 14 may be relayed to and utilized by cooling fluid source 30 for controlling the supply of cooling fluid to electrode assembly 20 in accordance therewith. Other configurations of contact(s) or similar features for establishing electrical communication and electrical energy transmission between handle assembly 14 and electrode assembly 20 are also contemplated.

Electrode assembly 20 defines a longitudinal axis "X-X" and includes an electrically-conductive needle 24 having a proximal end, a distal end, and defining a hollow interior 28. An insulative sleeve 29 (or coating) is disposed about a portion of the external surface of needle 24, and, as mentioned above, one or more electrical contacts 22b is disposed on the proximal end of needle 24 and is configured to permit electrical coupling of needle 24 to handle assembly 14 upon mechanical engagement of electrode assembly 20 and handle assembly 14 to one another.

The proximal end of electrode assembly 20 is configured for insertion into engagement recess 18 of housing 16 of handle assembly 14 and includes a pair of outwardly-extending protrusions 21 (or other suitable complementary structure) configured to releasably engage notches 19 defined within engagement recess 18 of handle assembly 14 to releasably engage electrode assembly 20 within engagement recess 18 of handle assembly 40.

Continuing with reference to FIGS. 1-2, needle 24 extends distally from engagement recess 18 of housing 16 of handle assembly 14 and defines a distal tip 26 configured to facilitate the penetration of tissue while minimizing the risk of hemorrhage from the puncture tract, although other distal tip configurations are also contemplated. Needle 24 is formed from an electrically-conductive material of which at least distal tip 26 is exposed. An insulating sleeve 29, or coating of material, surrounds the remaining portion of needle 24 that extends distally from engagement recess 18. With at least distal tip 26 of needle 24 exposed, energy, e.g., RF energy, can be delivered from needle 24 to surrounding tissue to treat, e.g., ablate, tissue, as will be described further below.

One or more fibers 500a, 500b are associated with electrosurgical system 10. Fibers 500a, 500b may be optical sense fibers, such as phosphate glass fibers, or may be any suitable type of light transmissive member or optical member, and are configured to transmit light from a light source. Fibers 500a, 500b may be disposed on, within or attached to one probe 12, as will be described further below.

Fibers 500a, 500b sense a set of physical parameters, e.g., temperature and mechanical strain, within the needle 24 and other components of the probe 12 and may provide identification information of the probe 12 to the generator 40. Fibers 500a, 500b are configured to detect changes in a set of physical parameters of the probe 12. In this manner, fibers 500a, 500b act as a sensor assembly, and may be coupled with a light source as described above. The generator 40 also includes an interrogator 41a coupled to the fibers 500a, 500b that decodes the optically encoded strain information from fibers 500a, 500b into electrical signals compatible with the computer control hardware of the generator 40. The generator 40 includes a controller 41b that is used to calculate temperature and forces exerted on the fibers 500a, 500b based on a formula, as will be described further below. The controller 41b may be any suitable type of logic circuit, such as field programmable gate array, processor, and the like. The generator 40 also includes a receptacle 45 (FIG. 1) configured to interface with the connector 43.

Figure 3:
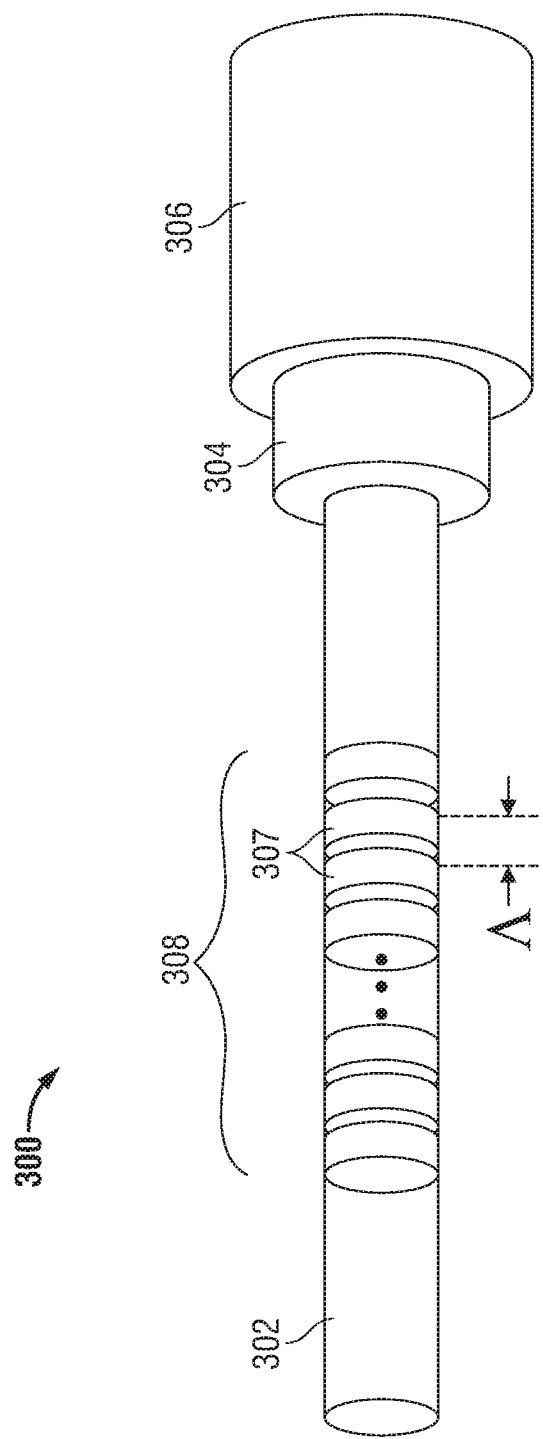
FIG. 3 is a perspective view of an optical fiber according to the present disclosure.

With reference now to FIG. 3, the fibers 400 (FIG. 4), 500a, 500b are described with respect to a fiber 300 to avoid repetition. The fiber 300 includes a core 302, a cladding 304 disposed over the core 302, and a buffer coating 306 covering the cladding 304. The fiber 300 also includes one or more fiber Bragg gratings (FBG) 308. Multiple gratings 308 may be written, e.g., etched, into the fiber 300 if the gratings 308 are formed in such a way as to use different wavelengths. This is particularly useful for using a single fiber 300 to sense multiple locations within the electrosurgical system 10. In further embodiments, multiple fibers 300 may be included each having one or more gratings 308.

The gratings 308 include a plurality of reflection points 307 written into the fiber 300 at periodic spacing "Λ." In some embodiments, the grating 308 may be written into the fiber 300 using high intensity pulses from a laser (e.g., argon fluoride excimer laser with a phase mask). As the fiber 300 undergoes mechanical strain (e.g., a change in length) due to temperature and pressure changes, the spacing Λ is modified due to stretching or contraction of the fiber 300. The effects of pressure and temperature are quantified by measuring the wavelength shift in light reflected by the reflection points 307 based on the formula (I), which is reproduced below:

$$\frac{\Delta \lambda}{\lambda_0} = k * \varepsilon + \alpha_\delta * \Delta T \quad (I)$$

In formula (I), $\Delta\lambda$ is the wavelength shift, $\lambda_0$ is the base wavelength, k is a gage factor, which is a difference between 1 and a photo-elastic coefficient, $\rho$, $\varepsilon$ is strain, $\Delta T$ is a temperature change, and $\alpha_\delta$ is a change of the refraction index.

In this manner, fiber 300 is configured to transmit at least one wavelength of light and to reflect at least one wavelength of light. Thus, the light transmissive properties, namely transmittance, of the fiber 300 corresponds to a set of physical parameters of the probe 12, and the light transmissive properties of the fiber 300 may transition with changing physical parameters or a changed condition of the probe 12. In particular, changes in temperature and pressure affect (e.g., stretch or contract) the fiber 300, which, in turn, modifies the spacing between the gratings 308. The change in the gratings 308 affects the wavelength of the light reflected back through the fiber 300. The change in the wavelength is then used by a controller (e.g., interrogator 41a of FIG. 1) to determine the change in temperature and/or strain affecting the fiber 300.

Figure 4:
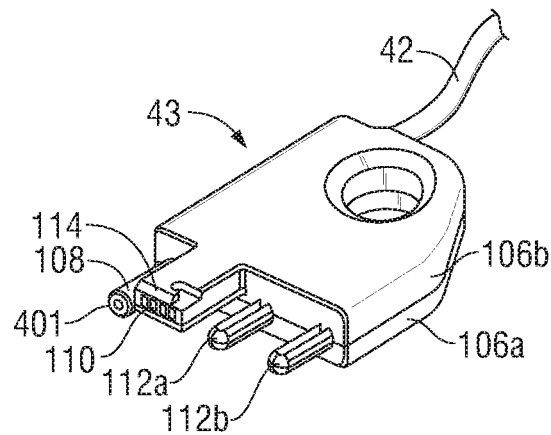
FIG. 4 is a perspective view of a connector according to an embodiment of the present disclosure.
Figure 5:
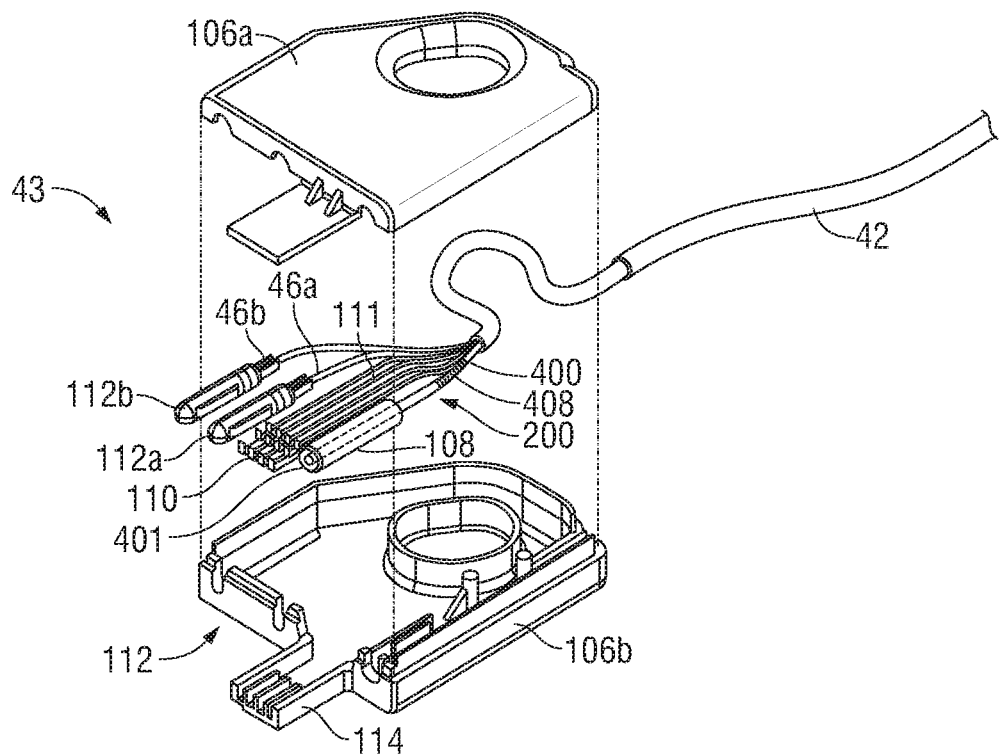
FIG. 5 is an exploded, perspective view of the connector of FIG. 4 according to an embodiment of the present disclosure.

With additional reference to FIGS. 4 and 5, an embodiment of connector 43 is shown coupled to cable 42 and includes a housing portion 106 having a first-half section 106a and a second half-section 106b operatively engagable with one another. Half-sections 106a, 106b are configured and adapted to retain an active pin 112a, a return pin 112b, an optical coupler 108, and a plurality of electrical contacts 110 disposed on a prong 114. Pin 112a is coupled to the wire 46a and the pin 112b is coupled to the wire 46b. The electrical contacts 110 are coupled to control leads 111 which may be coupled to various electrical controls, e.g., a switch. The optical coupler 108 is connected to a fiber 400 at a proximal end 401 of the fiber 400. Fiber 400 is substantially similar to fiber 300 discussed above. The receptacle 45 includes corresponding connectors for coupling the pins 112a, 112b, contacts 110, and optical coupler 108 to the generator 40, namely, energy-generating components (e.g., RF output stage), sensor circuits, the interrogator 41a, and the controller 41b.

The connector 43 includes an identification assembly 200 including the fiber 400, which includes a fiber Bragg grating 408 at a proximal end 401 thereof. The proximal end 401 of the optical fiber 400 which includes the fiber Bragg grating 408 is mounted loosely within the housing 106 of the connector 43 such that strain does not transfer to the fiber 400. In some embodiments, the fiber 400 may be thermally insulated (e.g., potting of the housing 106) to prevent thermal effects of the fiber Bragg grating 408. This configuration allows the fiber Bragg grating 408 to be unaffected by thermal fluctuations and mechanical strain imposed on the connector 43. Accordingly, the fiber Bragg grating 408 provides the same feedback when interrogated by the interrogator 41a. The fiber Bragg grating 408 may be individually tailored to encode identification information corresponding to a specific device (e.g., probe 12). The identification information that may be encoded in the fiber Bragg grating 408 may include, but is not limited to, serial number, model number, usage settings, configuration settings, and the like. Different identification information may be encoded by varying the number, thickness and periodic spacing between reflection points of the fiber Bragg grating 408. The interrogator 41a may interrogate the identification assembly 200 upon insertion of the connector 43 into the receptacle 45. Interrogation may be triggered by detection of the insertion using one or more proximity switches, limit switches, radio frequency tags, and the like.

Figure 6:
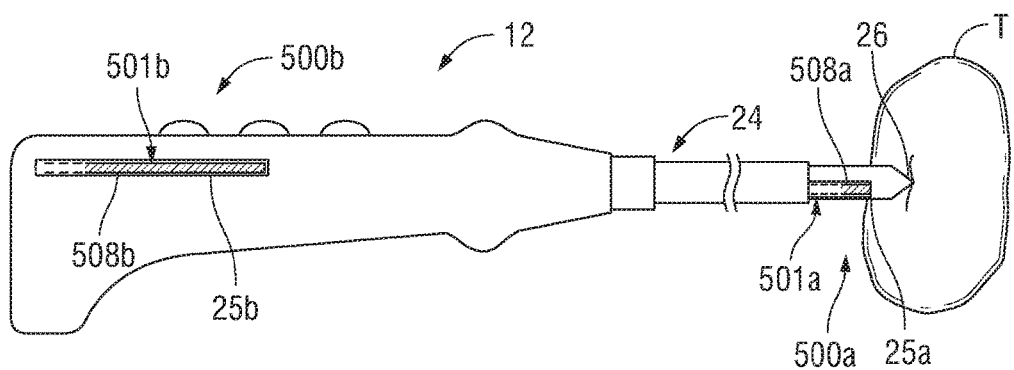
FIG. 6 is a front view of the generator of FIG. 1.

Turning to FIG. 6, use of probe 12 will be described in detail. Probe 12, lead by distal tip 26 of needle 24, is inserted into a site "T" such that exposed distal tip 26 of needle 24 of probe 12 is positioned adjacent to or within a target tissue to be treated, e.g., ablated. Tissue T may be any desired tissue site to be treated, e.g., a tumor or a diseased portion of tissue. In some embodiments, a treatment medium, e.g., a drug or wound closure fluid, may be disposed within the hollow interior 28 (FIG. 2) of needle 24, and may be delivered through the needle 24 into tissue T.

A return pad or return electrode (not shown) may, at this point or prior to, be operatively-adhered to or connected to the patient. With exposed distal tip 26 of needle 24 in position, energy, e.g., RF, microwave, laser, ultrasound, or thermal energy, is delivered from generator 40 to needle 24 and current is conducted from exposed distal tip 26 of needle 20 through the target tissue T, ultimately to be collected by the return electrode (not shown). An effective amount of energy at an effective energy level and for an effective duration of time is delivered to tissue T and controls may be provided on handle assembly 14 for controlling the supply of energy to needle 24 (not shown), or, alternatively, the supply of energy may be automatically or manually controlled by generator 40.

As the probe 12 is inserted through tissue T, needle 24 or other portions of probe 12 may encounter resistance to movement and may be subject to tensile, compressive, bending, and/or torsional forces as the probe 12 navigates tissue T. Further, the probe 12 and surrounding tissue T may experience a change in temperature with the application of energy to tissue T.

As described above, the probe 12 includes fibers 500a, 500b. The first fiber 500a is disposed in a first channel 25a defined in the probe 12 near needle 24. The second fiber 500b is disposed in a second channel 25b spaced away from the first channel 25a. The second channel 25b may be disposed within a portion of the needle 24 or may be disposed within another portion of the probe 12, e.g., handle assembly 14, and spaced away from the channel 25a. In some embodiments, the probe 12 may be formed or molded about the fibers 500a, 500b.

The fibers 500a and 500b include distal ends 501a, 501b, respectively, which are disposed within the first and second channels 25a, 25b of the probe 12. Each of the fibers 500a, 500b includes one or more fiber Bragg gratings 508a, 508b disposed within first and second channels 25a, 25b, respectively. The first and second channels 25a, 25b may be filled with thermally and electrically conductive material. The material may be a liquid such as saline. When light is projected through fibers 500a, 500b, both of the fiber Bragg gratings 508a, 508b, measure temperature at or near the probe 12. First fiber 500a is disposed within the probe 12. In particular, the fiber 500a is securely mounted within the channel 25a of probe 12, e.g., glued thereto or otherwise secured along the entire length thereof, to provide strain measurements imposed on the probe 12. Strain measurements allow for determination of pressure exerted on the probe 12. However, the gratings 508a are affected by both temperature and strain. To obtain accurate strain measurements at or near the probe 12, fiber 500b is mounted in a less secure manner to probe 12 (e.g., only at the distal end 501b within channel 25b, or mounted along an outer portion of probe 12) such that strain does not transfer to the fiber 500b. This configuration allows the fiber 500b to be affected only by changes in temperature.

Thus, the fiber 500a provides sensor feedback regarding a changed condition of probe 12, e.g., changes in temperature and mechanical strain, to the interrogator 41a while the fiber 500b only provides temperature feedback. The temperature feedback from the fiber 500b is used by the interrogator 41a and/or the controller 41b to determine the temperature at the probe 12 and the tissue site as well as the strain by correcting the feedback from the fiber 500a using the feedback from the fiber 500b. The feedback signal from the fiber 500b is used to remove the temperature component of the feedback signal from the fiber 500a to obtain the strain component. In this manner, measuring a first wavelength of light transmitted through the fibers 500a, 500b, forcing the probe 12 into contact such that a force is exerted on the fibers 500a, 500b causing a change in spacing between the Bragg gratings 508a, 508b, and measuring a second wavelength of light transmitted through the fibers 500a, 500b allows a comparison of the changed spacing between the Bragg gratings 508a, 508b indicative of mechanical strain and temperature changes.

Temperature and strain feedback from fibers 500a, 500b may be used by the controller 41b (FIG. 1) to control the output of the generator 40. In some embodiments, the adjustments to the output of the generator 40 may include, but are not limited to, changing modes (e.g., ablation, cutting, coagulation, sealing), changing power level (e.g., voltage and/or current), duty cycle, terminating energy, and combinations thereof. This reading may be provided to the generator 40, which may continuously display the resulting strain readings as pressure imposed on the probe 12 and tissue. In some embodiments, the generator 40 may output an indication that a predetermined pressure has been reached. This indication may be used as one of the conditions in determining whether a tissue seal or target ablation volume is complete. Additionally, this feedback may be used to indicate a depth of insertion of the probe 12 into tissue T. In some embodiments, a baseline value may be established (e.g., placement of the probe 12 at a skin surface or just above tissue T) and a change in this value may be indicated by the fibers 500a, 500b (e.g., insertion of the probe 12 to a predetermined depth, or complete withdrawal from tissue T) may cause a shutdown of the generator 40 or the entire electrosurgical system 10.

Additionally, during an electrosurgical procedure, the characteristics of the tissue T may change such that the tissue T may resist movement of the probe 12 differently. For example, charred tissue will be relatively tougher and have a tendency to resist movement. In some embodiments, the three-dimensional strain in the x, y, z coordinates, i.e., the ratio of the deformation of particular points within the probe 12 relative to the original positioning of those points within the probe 12, will provide a mechanism to monitor and regulate the effects of the needle 24 upon the tissue T.

Figure 7:
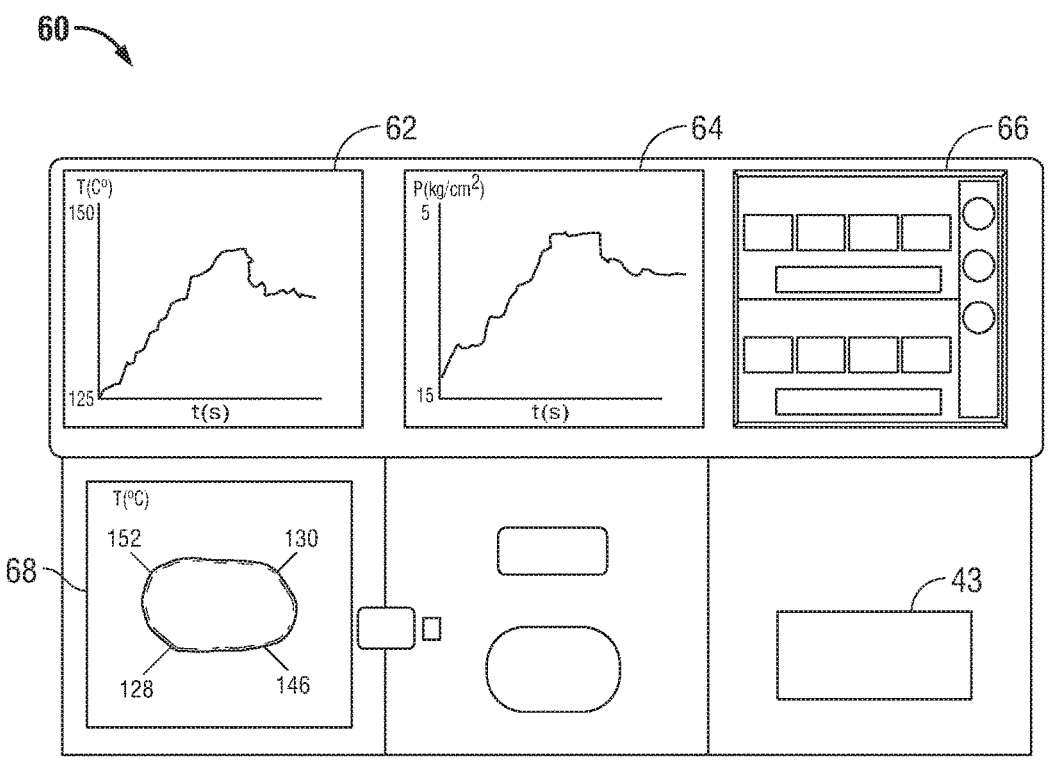
FIG. 7 is a side view of the probe of FIG. 1 being inserted into a tissue site.

Turning to FIG. 7, and as described above, and as described above, generator 40 may include a display system 60. Specifically, the display system 60 may be coupled to the interrogator 41a and/or the controller 41b (FIG. 1). Display system 60 may include a monitor or a graphic touchscreen display, as well as switches and illuminated indicators. Further, the controller 41b may be configured to execute algorithms for converting raw strain and temperature signals into one or more processed data, e.g., pressure measurements. In some embodiments, the display system 60 may include controls 66 allowing an operator to cycle through multiple display screens.

The display system 60 displays a graphical representation of the performance of probe 12 or another surgical device. This graphical representation may include an image corresponding to the temperature and/or strain readings captured by the interrogator 41a and/or controller 41b. As shown, display system 60 may display a measured temperature or applied pressure by the probe 12 over a time interval. Such a temperature gauge 62 may be measured over a range of, e.g., 0 to 150 degrees Celsius, and a pressure gauge 64 may be measured over a range of, e.g., 0 to 16 kg/cm$^2$. In some embodiments, the display system 60 may also display instantaneous pressure and/or temperature values. In further embodiments, display system 60 may display pressure and temperature in various real-time and graphical representations, such as bar graphs, which may be color-coded to represent the magnitude of pressure and temperature readings (e.g., red to represent high temperature and/or pressure, yellow to represent intermediate temperature and/or pressure, and green to represent low temperature and/or pressure, and combinations thereof). In this manner, display system 60 may provide a real-time pressure applied to tissue T by an operator as well as the thermal conditions at the tissue T. With this direct feedback, an operator may choose to alter or discontinue an electrosurgical procedure accordingly. Further, an operator may use the display system 60 to choose another surgical instrument or a differently sized or configured probe 12 with which to perform an electrosurgical surgical procedure.

Figure 8:
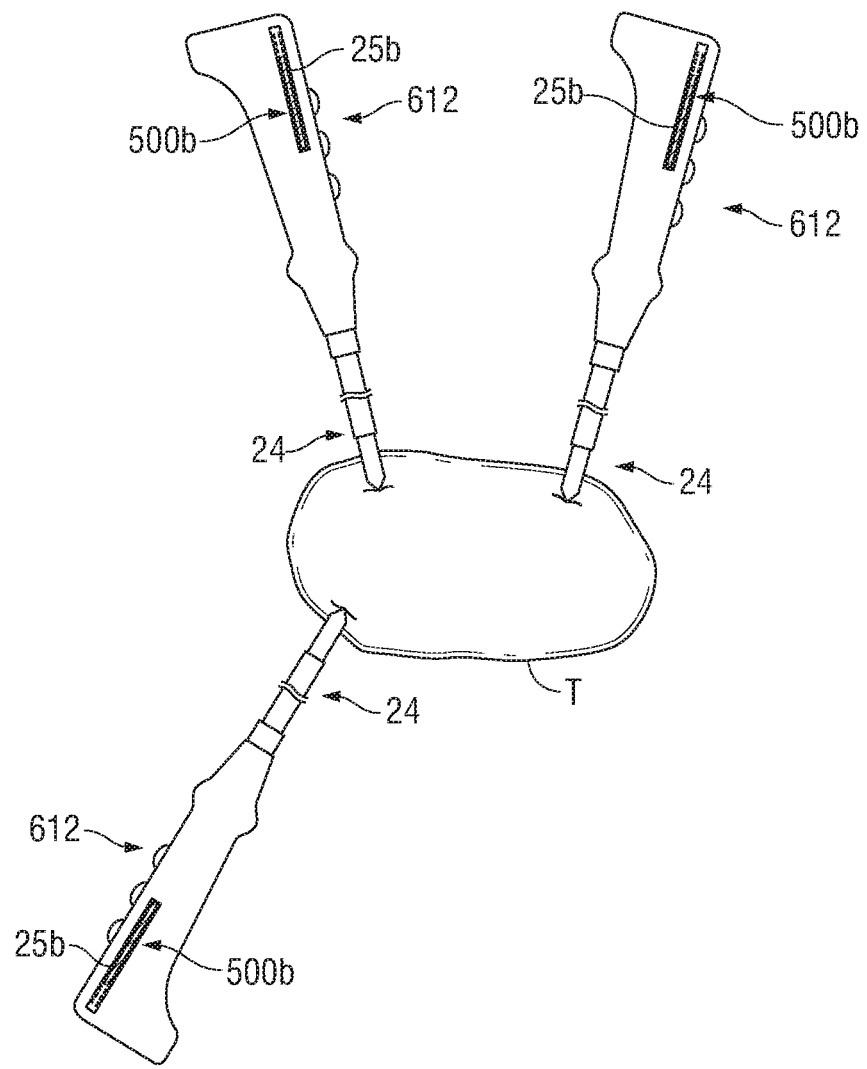
FIG. 8 is a side view of a plurality of probes of FIG. 1 being inserted into a tissue site according to an embodiment of the present disclosure.

Referring to FIG. 8, according to another embodiment of the present disclosure, a plurality of probes 612 may be introduced into tissue site T. Probes 612 are substantially similar to probe 12 described above, and in some embodiments, may be devoid of an electrode or electrical contacts to deliver RF energy to tissue site T. Additionally, needle 24 may or may not include a hollow interior. Probes 612 are configured to be inserted into tissue site T in the manner described above. Probes 612 may be inserted into different portions of tissue site T such that an array of probes 612 are associated with and are disposed within different and spaced apart portions of tissue T.

Each of the probes 612 includes at least fiber 500b to measure temperature at the tissue site T. Accordingly, fiber 500b may be mounted in channel 25b in a portion of probe 612 that does not experience mechanical strain, or channel 25b may be filled with a fluid medium to buffer fiber 500b from mechanical strain experienced by probe 612, as described above. In this manner, the plurality of probes 612 are configured to detect a plurality of changing conditions of the respective probes 12. In some embodiments, probes 612 may additionally include fiber 500*a* disposed in a portion of probe 612 that experiences mechanical strain.

With the varied placements of probes 612 in tissue site T, temperature variations across tissue site T may be measured by fibers 500*b*. Accordingly, a thermal profile or thermal map 68 (FIG. 7) of tissue site T may be provided by fibers 500*b* of probes 612. The thermal map 68 of tissue site T may be displayed on display system 60 in the manner described above. Accordingly, an operator may view such a thermal map to determine the course of an electrosurgical treatment in instances where an irregular thermal profile is desired at tissue site T. Further, the volume of tissue site T may be determined by supplying a known heat quantity to tissue site T and measuring the temperature changes across spaced apart points of tissue T. Those skilled in the art of the present disclosure will envision other uses for thermal data provided by probes 612.

Figure 9:
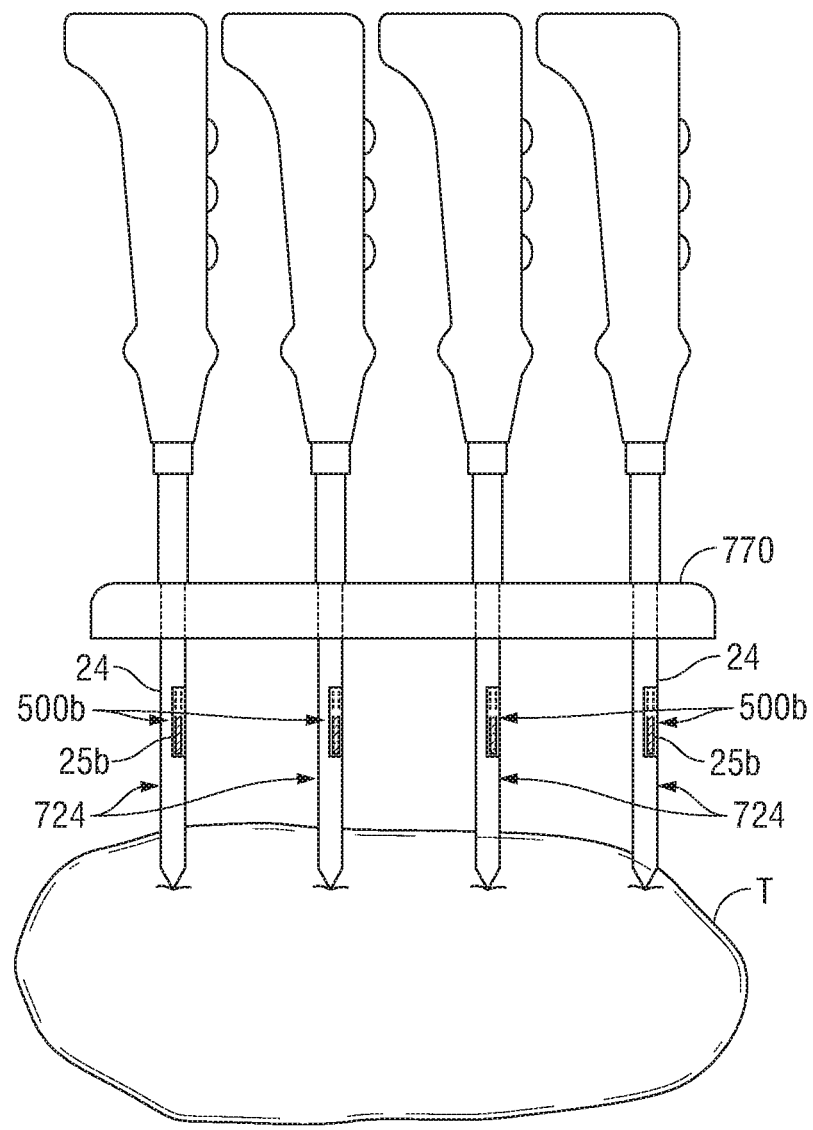
FIG. 9 is a side view of a plurality of needles of FIG. 1 extending from a hub and being inserted into a tissue site according to an embodiment of the present disclosure.

Turning to FIG. 9, in another embodiment of the present disclosure, needles 724 may be uncoupled from respective handle assemblies 14 (FIG. 2) and extend into tissue site T from a guide member, template, or hub 770. Needles 724 may be inserted through or secured to hub 770. Needles 724 are substantially similar to needles 24 discussed with respect to previous embodiments, though may be devoid of an electrode or electrical contacts to deliver RF energy to tissue site T. Additionally, needles 724 may or may not include a hollow interior. The needles 724 include at least one fiber 500*b* attached along the length thereof or otherwise secured to needles 724. Fiber 500*b* is isolated from mechanical strain induced by the insertion of needles 724 into tissue T. Accordingly, fiber 500*b* is configured to measure only temperature at tissue site T. In some embodiments, needles 724 may include additional fibers for detecting mechanical strain. Needles 724 are configured to generate a thermal map 68 (FIG. 7) in the manner described above with respect to probes 612.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Although the foregoing disclosure has been described in some detail by way of illustration and example, for purposes of clarity or understanding, it will be obvious that certain changes and modifications may be practiced within the scope of the appended claims.

What is claimed is:

1. A method of determining tissue characteristics based on engagement with an electrosurgical device, the method comprising:
    inserting an electrosurgical device into an object, the electrosurgical device having an electrode assembly and a light source configured to transmit light through an optical member at least partially disposed within a portion of the electrode assembly;
    measuring a first wavelength of light transmitted through the optical member;
    applying electrical energy to the electrode assembly;
    measuring a second wavelength of light transmitted through the optical member; and
    comparing the first wavelength of light to the second wavelength of light to determine a change in spacing between a plurality of segments of the optical member resulting from applying the electrical energy to the electrode assembly.

2. The method of claim 1, wherein comparing the first wavelength of light to the second wavelength of light includes determining a change in temperature of the electrode assembly.

3. The method of claim 1, wherein comparing the first wavelength of light to the second wavelength of light includes determining at least one of a change in temperature or a change in mechanical strain on the electrode assembly.

4. The method of claim 1, wherein the electrosurgical device includes a plurality of electrode assemblies.

5. The method of claim 4, further comprising comparing for each of the electrode assemblies comparing the first wavelength of light to the second wavelength of light.

6. The method of claim 5, further comprising generating a thermal profile based on comparing the first wavelength of light to the second wavelength of light for each of the electrode assemblies.

7. An electrosurgical device, comprising:
    an electrode assembly;
    a light source configured to transmit light through an optical member at least partially disposed within a portion of the electrode assembly;
    a sensor disposed along the electrode assembly configured to measure wavelengths of light transmitted through the optical member; and
    a controller in electrical communication with the optical member and the sensor, the controller configured to:
        receive a first sensor signal based on a first wavelength of light transmitted through the optical member,
        transmit a control signal to an electrosurgical generator coupled to the electrosurgical device to apply electrical energy to the electrode assembly,
        receive a second sensor signal based on a second wavelength of light transmitted through the optical member; and
        compare the first wavelength of light to the second wavelength of light and determine a change in spacing between a plurality of segments of the optical member resulting from applying the electrical energy to the electrode assembly.

8. The electrosurgical device of claim 7, wherein comparing the first wavelength of light to the second wavelength of light includes determining a change in temperature of the electrode assembly.

9. The electrosurgical device of claim 7, wherein the electrosurgical device includes a plurality of electrode assemblies.

10. The electrosurgical device of claim 9, wherein the controller is further configured to compare the first wavelength of light to the second wavelength of light for each of the respective electrode assemblies.

11. The electrosurgical device of claim 10, wherein the controller is further configured to generate a thermal profile based on the first wavelength of light and the second wavelength of light of each of the electrode assemblies.

12. A method of measuring characteristics of an electrosurgical device, the method comprising:
    projecting light from a light source of an electrosurgical device through an optical member at least partially disposed within an electrode assembly of the electrosurgical device;
    measuring a first wavelength of light transmitted through the optical member;

inserting at least a portion of the electrode assembly into an object such that a force is applied to the electrode assembly;

measuring a second wavelength of light transmitted through the optical member while the force is applied; and comparing the first wavelength of light to the second wavelength of light to determine a change in spacing between a plurality of segments of the optical member resulting from the force.

13. The method of claim 12, wherein comparing the first wavelength of light to the second wavelength of light includes determining a change in temperature of the electrode assembly.

14. The method of claim 12, wherein comparing the first wavelength of light to the second wavelength of light includes determining at least one of a change in temperature or a change in mechanical strain on the electrode assembly.

15. The method of claim 12, wherein projecting light includes projecting light through a plurality of optical member at least partially disposed within respective electrode assemblies of the electrosurgical device.

16. The method of claim 15, wherein comparing the first wavelength of light to the second wavelength of light includes comparing the first wavelength of light to the second wavelength of light of each of the electrode assemblies.

17. The method of claim 16, further comprising generating a thermal profile based on comparing the first wavelength of light to the second wavelength of light for each of the electrode assemblies.

* * * * *